United States Patent [19]
Point

[11] Patent Number: 6,068,476
[45] Date of Patent: May 30, 2000

[54] SALIVA EJECTOR WITH ATTACHED COVER-SLIP

[76] Inventor: Catherine L. Point, 847 Woodside Way, San Mateo, Calif. 94401

[21] Appl. No.: 09/337,044

[22] Filed: Jun. 21, 1999

[51] Int. Cl.[7] .................................................. A61C 17/06
[52] U.S. Cl. ............................................ 433/96; 604/171
[58] Field of Search ...................... 433/91, 96; 600/121, 600/122; 604/171, 263

[56] References Cited

U.S. PATENT DOCUMENTS

| | | | |
|---|---|---|---|
| 1,060,665 | 5/1913 | Bell | 604/181 |
| 4,772,275 | 9/1988 | Erlich | 604/263 |
| 4,810,194 | 3/1989 | Snedden | 433/91 |

FOREIGN PATENT DOCUMENTS

| | | | |
|---|---|---|---|
| 570255 | 11/1993 | European Pat. Off. | 433/91 |

Primary Examiner—Ralph A. Lewis
Attorney, Agent, or Firm—Feix & Feix

[57] ABSTRACT

A disposable saliva ejector assembly for use in connection with a vacuum source for withdrawing saliva and bioburden from the oral cavity of a dental patient. The saliva-ejector assembly includes a flexible hollow tube having a first end provided with a suctioning tip and a second end adapted for connecting to a vacuum source. The assembly further includes a flexible plastic cover-slip having a first end fixedly attached to the tube at a distance inwardly of the tube second end sufficient to permit a friction fit connection between the tube second end and a tube receiving fixture of the vacuum source, and a second free end. The cover-slip is adapted to be movable between a first, pre-use position, wherein the cover-slip envelopes the tube with the second free end of the cover-slip extending beyond the suctioning tip, and a second, use position wherein the cover-slip is peeled inside out in order to expose the suctioning tip and to protectively cover the connection between the tube second end and the tube receiving fixture as well as a portion of vacuum tubing connected to said tube receiving tubing.

9 Claims, 6 Drawing Sheets

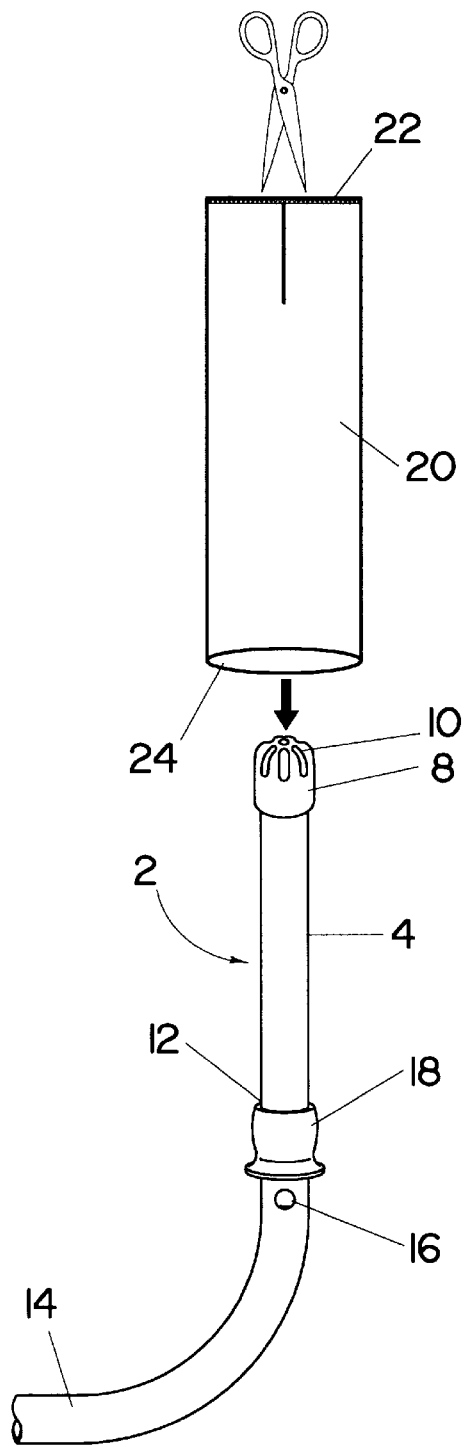
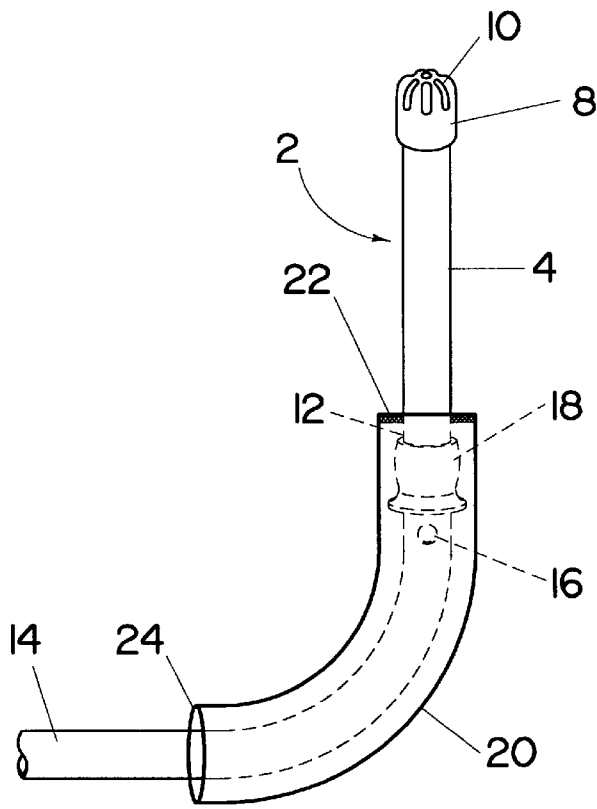
figure 2 (Prior Art)
figure 3 (Prior Art)

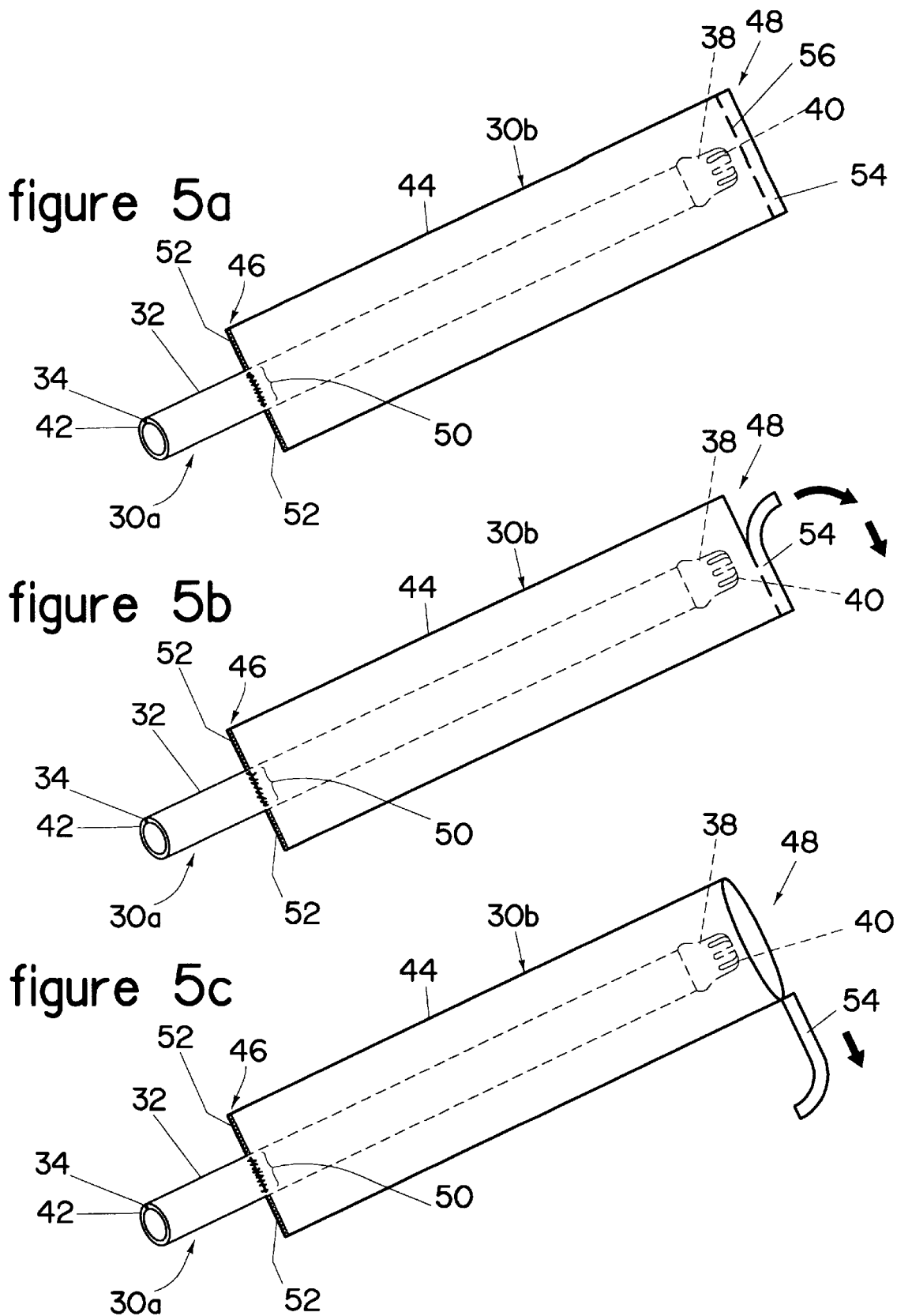

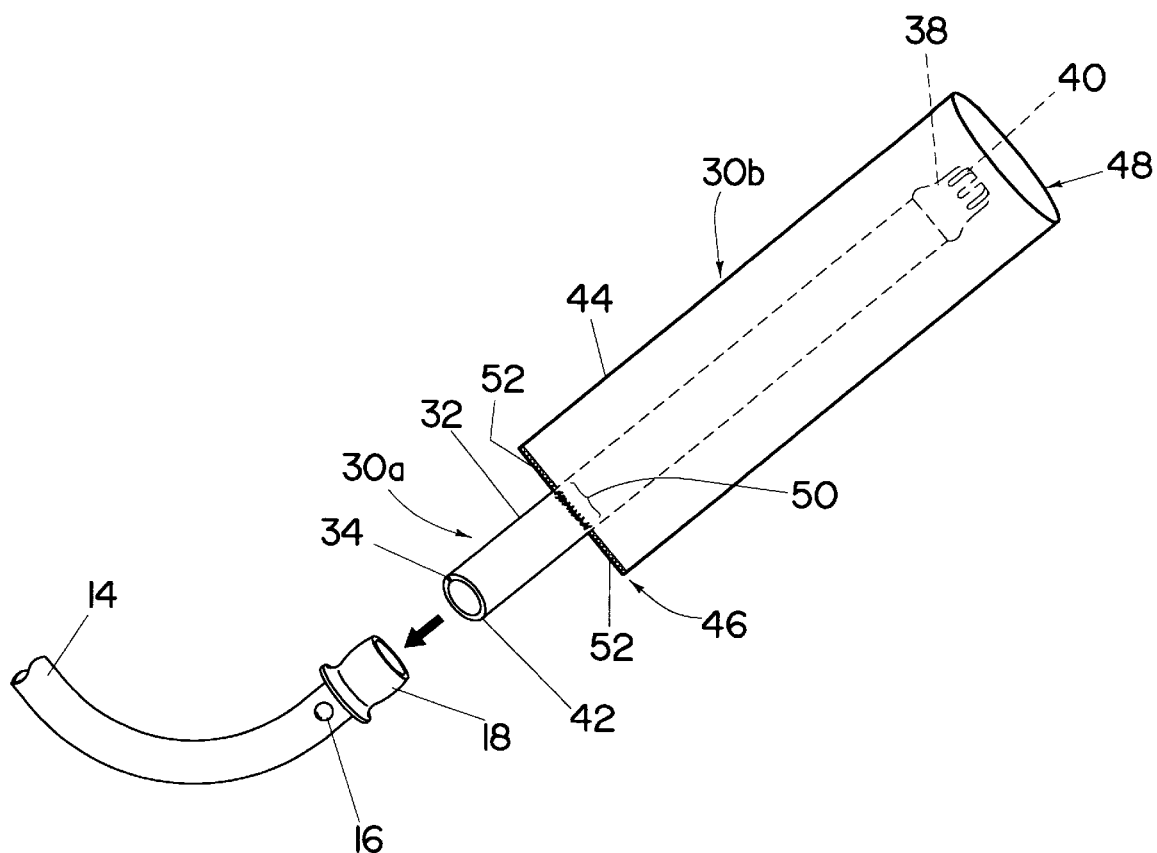

SALIVA EJECTOR WITH ATTACHED COVER-SLIP

TECHNICAL FIELD

The present invention relates to an improved disposable saliva ejector used in the field of dentistry. More specifically, the invention relates to an improved disposable saliva ejector having an attached cover-slip that is effective to protect against bacterial contamination of the suction tube of a dental aspirator system to which the disposable saliva ejector is removably fitted.

BACKGROUND OF THE INVENTION

A disposable plastic tube, called a saliva ejector, is used in combination with a suction tube of a dental aspirator system to suction saliva and bioburden during dental procedures. With reference to FIGS. 1 to 3, there is shown a disposable saliva ejector 2 in accordance with the prior art. The saliva ejector 2 comprises a bendable hollow tube 4 which includes a first end 6 having a suction tip 8 with open slits 10 for suctioning the oral cavity. The tube 4 further includes a second end 12 sized for close fit insertion into the receiving fixture 18 of suction tube 14 of a dental aspirator system. The suction tube 14 of the dental aspirator system typically has a suction control knob 16 disposed adjacent the receiving fixture or fitting 18. During a dental procedure, the hygienist will reposition the saliva ejector 2 in the patient's mouth many times by handling the region of the base area of the saliva ejector 2 and the receiving fixture 18. As a result of this handling, the suction tube 14 is subject to contamination by the transmission of bacteria from the patient's mouth via the hygienist's gloved hands. In accordance with OSHA recommendations, the connection between the saliva ejector 2 and the suction tube 14 should be covered with a plastic cover-slip 20 in order to prevent bacterial contamination of the suction tube 14.

In accordance with the conventional practice, once the disposable saliva ejector 2 is fitted to the suction tube 14, the dental hygienist must apply the cover-slip 20 to seal off this connection point. The prior art cover slip 20 is an elongated flat plastic sleeve having a closed end 22 and an open end 24. They are mass produced items and are shipped in bulk. Prior to use, each cover-slip 20 must be prepared by first retrieving the cover-slip 20 from its bulk packaging container and then cutting a hole in the closed end 22. The open end 24 of the cover-slip 20 is next guided over the saliva ejector 2 and pulled down to where the saliva ejector 2 joins the suction tubing 14. The desired final positioning of the cover-slip 20 over the saliva ejector 2 and suction tubing 14 is shown in FIG. 3.

The above described set up and preparation process is very time consuming. And since time is at a premium in the dental office, there is a need for an improved saliva ejector that accelerates the set up process for each dental procedure.

Another problem often encountered with the prior art plastic cover-slip preparation technique has to do with the size hole that is cut into the closed end 22 of the cover-slip 20. If the cut hole is too large in diameter, the cover-slip 20 has the tendency to slide down the suction tubing 14 beyond the receiving fixture or fitting 18 where it is supposed to protect the suction tube 14 and dental aspirator system from bacterial contamination. If the hole is too small, it tends to hang up and snag against the suction tip 8 of the saliva ejector 2. In many instances, the hygienist continues to pull on the cover-slip 20 in order to overcome the snag point thereby causing the cut hole to rip or tear unevenly, thus again making it too big and thus ineffective in preventing against bacterial contamination of the suction tube 14 and the rest of the dental aspirator system.

Even in the case where the hole is cut to the right size, there is still a tendency for the cover-slip 20 to bunch upwards upon handling since the separate plastic cover-slip is not firmly attached to any portion of the saliva ejector 2. A cover-slip 20 which bunches up upon handling must be repeatedly smoothed back down. This happens because the separate cover-slip 20 is placed over the saliva ejector 2 and suction tubing 14 via the hole cut in it, and currently, there is no means available provided by manufacturers of saliva ejectors to anchor or affix the cover-slip to the saliva ejector in order to prevent these types of problems from occurring. Therefore, it would be a streamlining advantage to have the cover-slip affixed to the saliva ejector, prior to use, at the site of manufacture.

To the best of my knowledge, I am not aware of any prior art that proposes a solution to the above-described problem. However, the following U.S. patents are considered to be relevant to the general state of the art: U.S. Pat. No. 5,688,121 issued Nov. 18, 1997 to Davis; U.S. Pat. No. 5,441,410 issued Apr. 8, 1993 to Segerdal; U.S. Pat. No. 5,076,787 issued Dec. 31, 1991 to Overmyer; and U.S. Pat. No. 4,221,220 issued Sep. 9, 1980 to Hansen.

SUMMARY OF THE INVENTION

Briefly, in accordance with a preferred embodiment, the present invention provides for an improvement to the prior art disposable saliva ejector, by attaching a separate cover-slip to it at the site of manufacture. The improved disposable saliva ejector with attached cover-slip reduces saliva ejector preparation time to a one-step process of inserting the saliva ejector with cover-slip attached into the suction tubing. This advantageously saves time and reduces inconvenience for dental personnel when setting up the dental operator. Rather than having to reach for a separate cover-slip, cut a hole in the closed-end, place it over the saliva ejector, and finally pull it down over the suction tubing, the saliva ejector with attached cover-slip of the present invention greatly expedites the setting up process.

In accordance with an advantageous aspect of the invention, the attached cover-slip may additionally serve as a hygienic envelope, protecting and keeping the saliva ejector's oral suctioning tip sanitary until use, which is an expanded advantage to having the cover-slip affixed to the saliva ejector, prior to use, at the site of manufacture. In other words, the attached cover-slip provides a dual function. Prior to use it serves as sanitary packaging for the saliva ejector and during use it serves as an antibacterial contamination guard for the dental aspirator system.

These and other features and advantages of the present invention will be apparent from the following description and claims and are illustrated in the accompanying drawings, which by way of illustration, show preferred embodiments of the present invention and the principles thereof and what are now considered to be the best modes contemplated for applying these principles. Other embodiments of the invention embodying the same or equivalent principles may be used and structural changes may be made as desired by those skilled in the art without departing from the present invention and the purview of the appended claims.

BRIEF DESCRIPTION OF THE DRAWINGS

FIG. 2 is a generally schematic view which illustrates the process of preparing a conventional plastic cover-slip for covering the connection between saliva ejector and suction tube fitting of FIG. 1.

FIG. 3 illustrates the final placement of the plastic cover-slip over the connection between saliva ejector and suction tube fitting of FIG. 1.

FIGS. 5a through 5c are a series of generally schematic views which illustrate the action of tearing off a tamper-proof removable seal provided as an additional feature to the embodiment of FIG. 4.

FIG. 6 is a generally schematic view of the saliva ejector with attached cover-slip being placed into a suction tube fitting of a dental aspirator system.

DETAILED DESCRIPTION OF THE PREFERRED EMBODIMENTS

Figure 1:
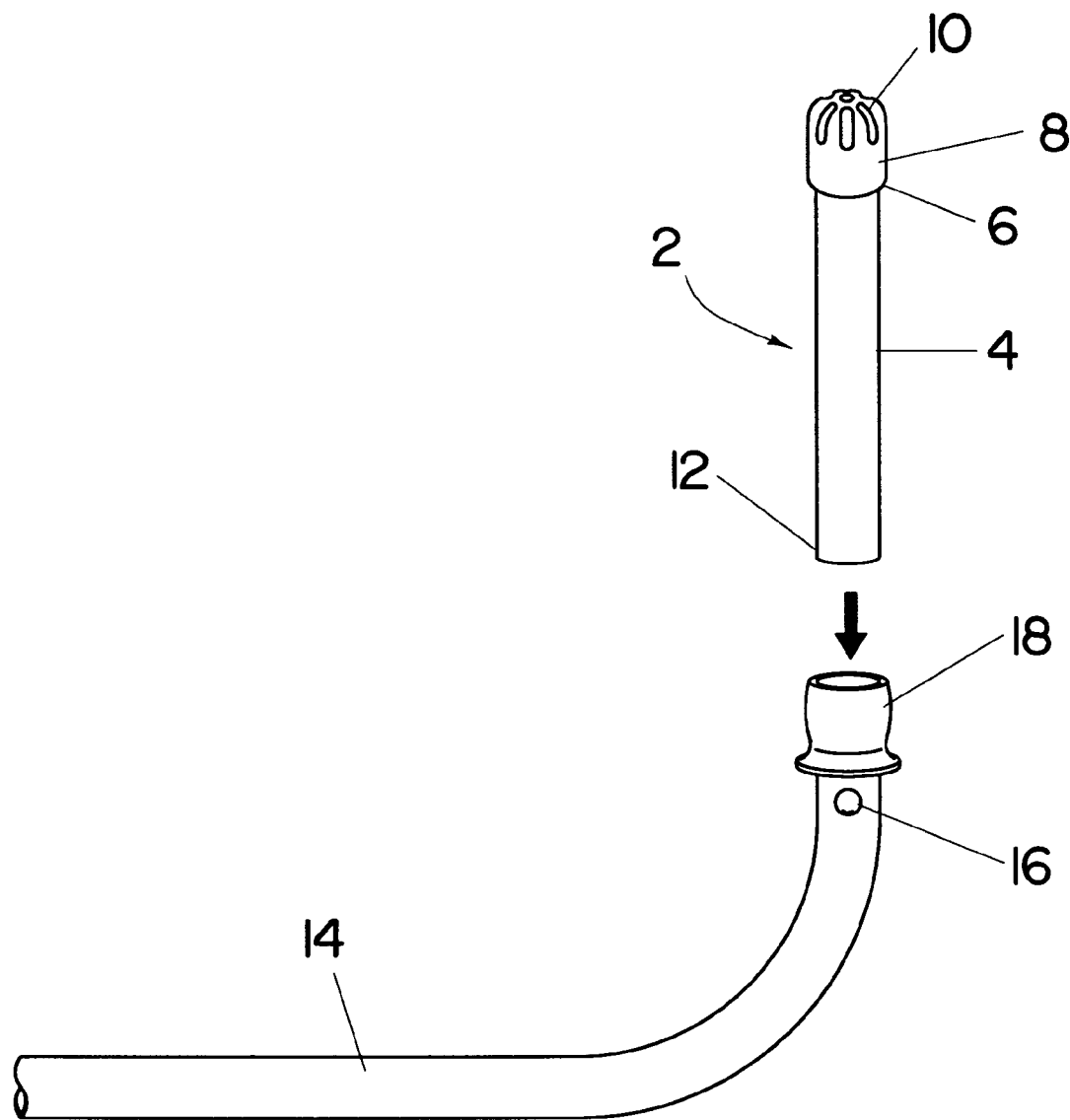
FIG. 1 is a generally schematic depiction of a prior art disposable saliva ejector being placed into the receiving fixture of a suction tube of a dental aspirator system.
Figure 4:
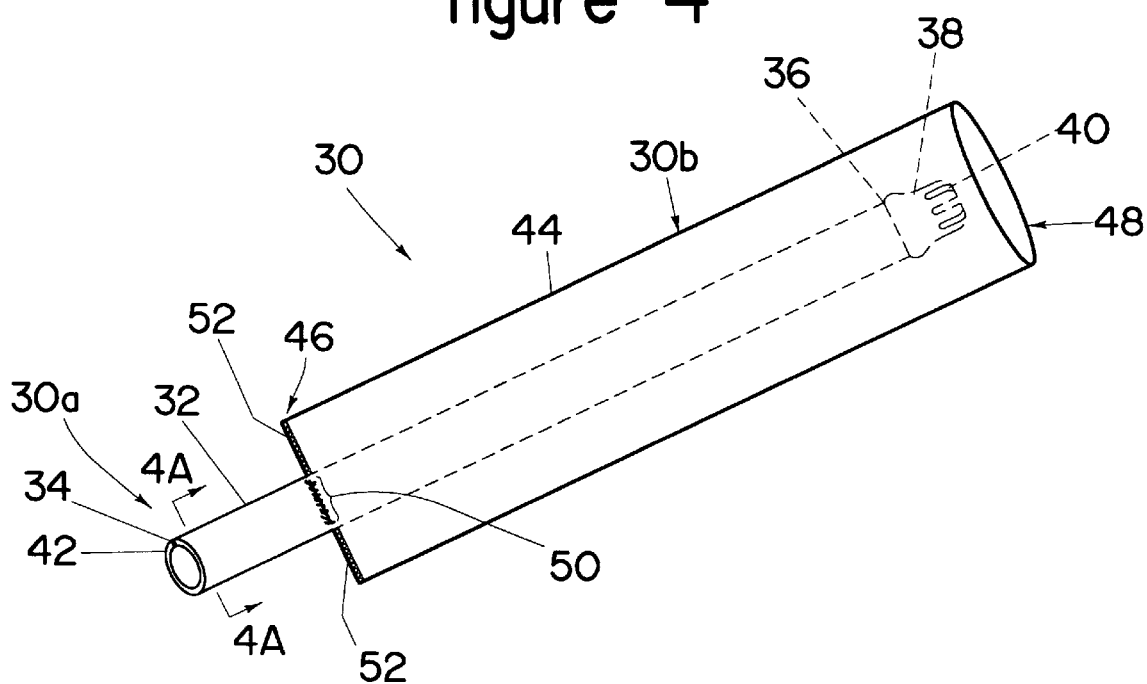
FIG. 4 illustrates a saliva ejector with attached cover-slip in accordance with the present invention.

A disposable saliva ejector with attached cover slip constructed in accordance with a preferred embodiment is designated generally by reference numeral 30 in FIGS. 4 and 6.

Figure 4A:
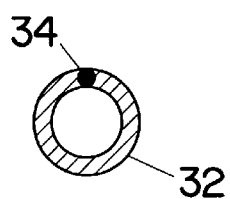
FIG. 4A is a cross section view of the saliva ejector taken along the line and in the direction of arrows 2—2 of FIG. 4.

More particularly, the invention comprises a saliva ejector portion 30a and a cover-slip portion 30b. The saliva ejector portion 30a is constructed of a bendable hollow tube 32 of approximately five and three quarter inches in length and one quarter inch in diameter. The hollow tube 32 is made of a semirigid, but flexible, plastic such as polyvinyl chloride (PVC) material. As best seen in FIGS. 4 and 4A, the tube 32 preferably also internally incorporates a thin bendable wire 34 into its sidewall that runs approximately the entire length of the tube 32. The bendable wire 34 enables the saliva ejector to hold a bent configuration to comfortably fit the mouth of the patient during a particular dental procedure.

The tube 32 includes a first end 36 having a suction tip 38 provided with open slits 40 for suctioning the oral cavity. The tube 32 further includes a second end 42 sized for close fit insertion into the receiving fixture or fitting 18 of suction tube 14 of a dental aspirator system (see FIG. 6). The suction tube 14 typically has a suction control knob 16 disposed adjacent the suction tube fitting 18.

The cover-slip portion 30b includes a plastic sleeve-like cover-slip 44 having a first end 46 affixed to the tube 32 at a location close to, but inwardly of, the tube second end 42, and a second end 48 which extends just beyond the suction tip 38 of the saliva ejector. Opposing wall panel portions of the first end 46 of the cover-slip 44 are affixed to the outer side wall of the tube 32 by seams 50 (only one of which is seen in the Figures). The seems 50 may be formed using a suitable adhesive or they may be formed using conventional heat sealing means. The portions of the cover-slip first end 46 on either side of tube 32 are sealed closed by sealed edges 52. The combination of seams 50 and sealed edges 52 provide a substantially air tight seal between the cover-slip and the tube 32.

In an alternate embodiment (not shown), one or both of seams 50 connecting the tube 32 to the cover-slip first end 46 may be omitted. Even in the case where both seams 50 are omitted, the sealed edges 52 of the cover-slip first end 46 provide adequate air sealing and resistance to movement between the cover-slip first end 46 and the tube 32.

In the embodiment shown in FIGS. 4 and 6, the cover-slip second end 48 is formed as an open end. If it was decided to provide the cover-slip second end 48 with a seal, such seal would be made in such a way as to be opened with ease.

The series of FIGS. 5A through 5C illustrate, by way of example, an embodiment of the present invention wherein the cover-slip second end 48 is formed as a closed or sealed end. The closed second end 48 is provided with a tamper proof removable seal 54 that is removed along perforated line 56 to provide access to the suction tip 38. The removable seal 54 may be in the form of a conventional tear or peal seal. The tear off action of the removable seal 54 is best seen with reference to FIGS. 5B and 5C. In this embodiment, the cover-slip 44 advantageously serves as packaging for the suction tip 38 and a large portion of tube 32. In addition, the provision of tamper-proof removable seal 54 to the cover-slip second end 48 assures the advantage of knowing that the saliva ejector is sanitary prior to use. To this end, the cover-slip 44 is preferably comprised of transparent or clear plastic material to enable inspection of the saliva ejector prior to use and to enable inspection of the control knob 16 during use. The cover-slip may also be tinted with transparent or see-through color coatings, for example light shades of blue and pink, for identification and/or promotional purposes.

In an alternate embodiment, the cover-slip second end 48 may be formed as a simple heat sealed closed end without a separate tear seal.

In accordance with yet another alternate embodiment wherein the clover-slip second end 48 is formed as a closed end, one or both seams 50 connecting the tube 32 and the cover-slip first end 46 may be omitted as an option.

Figure 7:
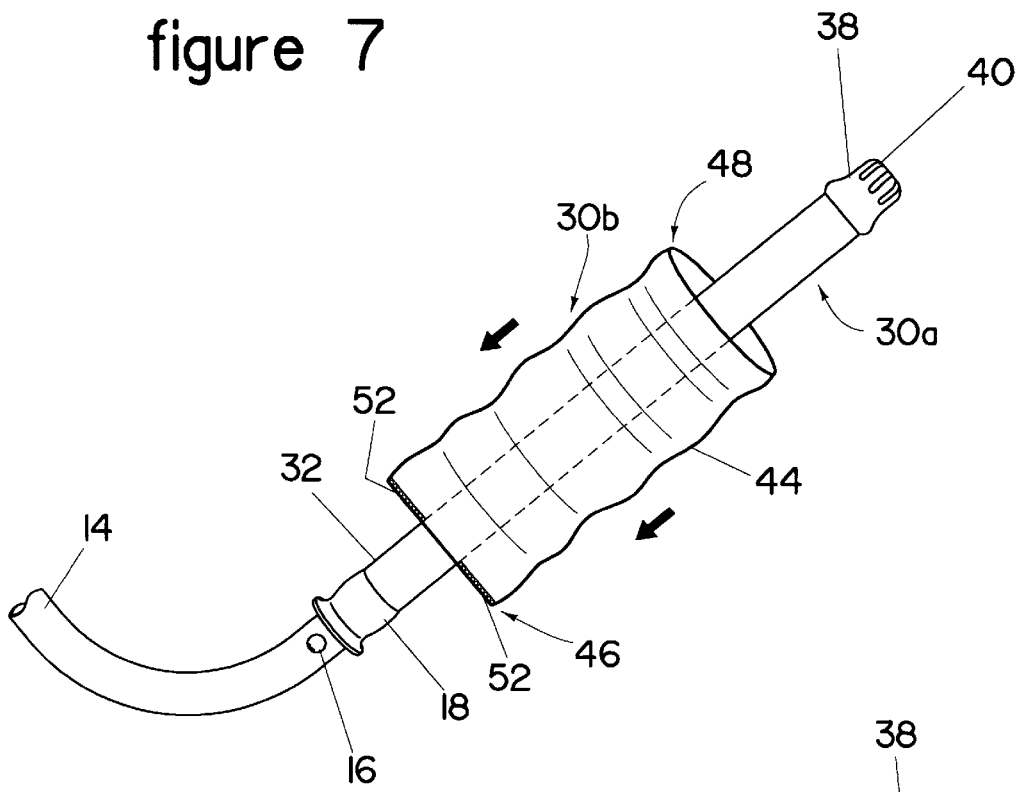
FIGS. 7 and 8 are generally schematic views similar to FIG. 6 which illustrate the attached cover-slip being pulled down over the saliva ejector to cover the connection between the saliva ejector, suction tube fitting, control knob and a portion of the suction tube.
Figure 8:
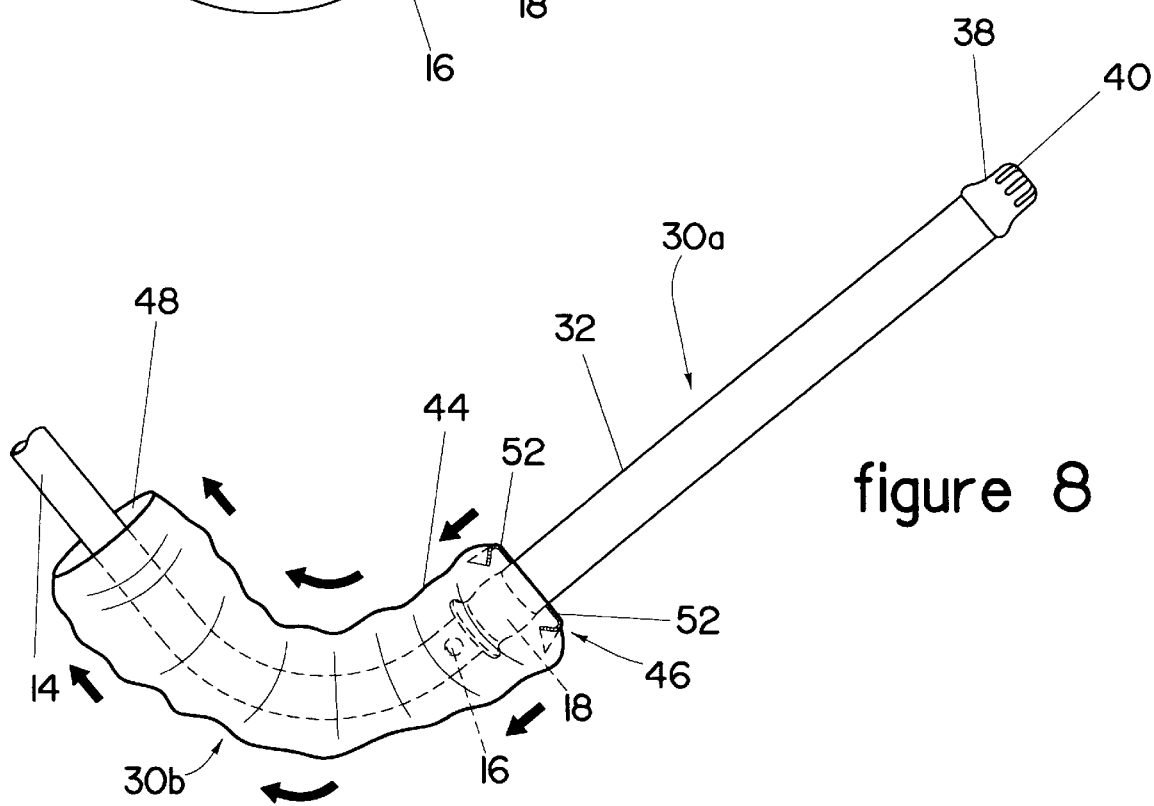

With reference now to FIGS. 7 and 8, once the second end 42 of tube 32 is inserted within suction tube fitting 18 and the cover-slip second end 48 is opened (i.e., in the case where cover-slip second end 48 is not pre-formed as an open end), the dental hygienist pulls the cover-slip second end 48 inside out in a direction towards the suction tube 14 until the cover-slip 44 is positioned over the fitting 18 and suction tube 14 as shown in FIG. 8. The sealed edges 52 of the cover-slip first end 46 together with the optional seams 50 effectively anchor the cover-slip first end 46 to the tube 32 of the saliva ejector 30a.

While I have illustrated and described the preferred embodiments of my invention, it is to be understood that these are capable of variation and modification, and I therefore do not wish to be limited to the precise details set forth, but desire to avail myself of such changes and alterations as fall within the purview of the following claims.

I claim:

1. A disposable saliva ejector assembly for use in connection with a vacuum source for withdrawing saliva and bioburden from the oral cavity of a dental patient, said saliva-ejector assembly comprising:

a) a flexible hollow tube including an initially sterilized tube first end provided with a suctioning tip and a tube second end adapted for connecting to a vacuum source;

b) a cover-slip made of thin flexible plastic material, wherein said cover slip includes:

i) a first end fixedly attached to said tube at a distance inwardly of said tube second end sufficient to permit a friction fit connection of said tube second end to a tube receiving fixture of said vacuum source;

ii) a second free end sealingly covering said sterilized tube first end; and iii) said cover-slip upon opening of said second free end adapted to be movable between a first, pre-use position, wherein said cover-slip envelopes said tube with said second free end extending beyond said suctioning tip, and a second, use position wherein said cover slip has been peeled inside out to expose said suctioning tip and to protectively cover said tube second end, said tube receiving fixture and a portion of vacuum tubing connected to said tube receiving tubing.

2. A disposable saliva-ejector assembly as in claim 1, wherein said tube has a tube wall incorporating a bendable wire that runs substantially the entire length of said tube, said bendable wire effective to retain said tube in a desired bend configuration for comfortably fitting within a patient's mouth during a particular dental procedure.

3. A disposable saliva-ejector assembly as in claim 1, wherein said second free end of said cover-slip includes a tamper-proof heat seal which is opened prior to moving said second free end to said second, use position.

4. A disposable saliva-ejector assembly as in claim 1, wherein the cover-slip comprises transparent material.

5. A disposable saliva-ejector assembly as in claim 4, wherein said transparent material is color tinted.

6. A disposable saliva-ejector assembly as in claim 1, wherein said second free end of said cover-slip includes a tear seal which is opened prior to moving said second free end to said second, use position.

7. In a dental aspirator system of the kind which includes a suction tube and a receiving fixture for mounting a removable a saliva ejector, a method of preventing contamination of the suction tube and receiving fixture caused by transmission of bacteria from a dental patient's mouth to the suction tube and receiving fixture resulting from the handling by a dental hygienist during a dental procedure, the method comprising the steps of:

a) providing a hollow, tubular saliva ejector having an initially sterilized first end provided with a suctioning tip and a second end adapted for connecting to the receiving fixture of the suction tube;

b) providing a cover-slip made of thin flexible material disposed around the saliva ejector, the cover-slip having a cover-slip first end fixedly attached to the saliva ejector at a distance inwardly of the saliva ejector second end sufficient to permit a friction fit connection of the saliva ejector second end to the receiving fixture of the suction tube, and a cover-slip second end sealingly covering the sterilized saliva ejector first end;

c) opening of the cover-slip second end; and d) peeling back the cover-slip inside out to expose the sterilized saliva ejector first end and to protectively cover the previously uncovered portion of the ejector tube second tube second end as well as the receiving fixture and a portion of the suction tube connected to the receiving fixture.

8. The method of claim 7 further including the step of providing the saliva ejector with an interiorly disposed bendable wire that extends along the length of the saliva ejector, the bendable wire being effective to retain the saliva ejector in a desired bend configuration for comfortably fitting within a patient's mouth during a dental procedure.

9. The method of claim 7 further including the step of forming the cover-slip of transparent material.

* * * * *